United States Patent [19]
Greaves et al.

[11] Patent Number: 5,976,570
[45] Date of Patent: Nov. 2, 1999

[54] METHOD FOR PREPARING LOW DOSE PHARMACEUTICAL PRODUCTS

[75] Inventors: Frank C. Greaves, Wilmington; James Swarbrick, Hampstead; Martin W. Beasley, Wilmington, all of N.C.; Andrew W. Suddith, Lawrence, Kans.; Henry C. Caldwell, Ambler, Pa.

[73] Assignee: Applied Analytical Industries, Inc., Wilmington, N.C.

[21] Appl. No.: 08/649,631

[22] PCT Filed: Dec. 20, 1994

[86] PCT No.: PCT/US94/14638

§ 371 Date: Jul. 15, 1996

§ 102(e) Date: Jul. 15, 1996

[87] PCT Pub. No.: WO95/17168

PCT Pub. Date: Jun. 29, 1995

[30] Foreign Application Priority Data

Dec. 21, 1993 [ZA] South Africa .......................... 93/9565

[51] Int. Cl.⁶ ..................................................... A61K 9/26
[52] U.S. Cl. ......................... 424/470; 424/489; 424/490; 424/465; 424/469
[58] Field of Search ..................... 424/470, 489, 424/490, 465, 469

[56] References Cited

U.S. PATENT DOCUMENTS

| | | | |
|---|---|---|---|
| 3,568,828 | 3/1971 | Lerner | 206/42 |
| 4,544,554 | 10/1985 | Pasquale | 514/170 |
| 4,684,534 | 8/1987 | Valentine | 424/3 |
| 5,211,958 | 5/1993 | Akkerboom et al. | 424/470 |
| 5,275,822 | 1/1994 | Valentine et al. | 424/489 |
| 5,395,627 | 3/1995 | Dopper et al. | 424/489 |

FOREIGN PATENT DOCUMENTS

| | | |
|---|---|---|
| 0 179 703 | 4/1986 | European Pat. Off. . |
| 0371466 | 11/1989 | European Pat. Off. . |
| 0 371 466 | 6/1990 | European Pat. Off. . |
| 0 503 521 | 9/1992 | European Pat. Off. . |

*Primary Examiner*—Thurman K. Page
*Assistant Examiner*—William E. Benston, Jr.
*Attorney, Agent, or Firm*—Finnegan, Henderson, Farabow, Garrett & Dunner, L.L.P.

[57] ABSTRACT

A process for making pharmaceutical dosage units containing a therapeutic quantity of one or more low dosage medicinal agent comprising granulating said medicinal agent in an aqueous medium which contains a pharmaceutically acceptable surfactant agent and, optionally, further processing the product of said granulating into a tablet or capsule dosage unit.

26 Claims, No Drawings

METHOD FOR PREPARING LOW DOSE PHARMACEUTICAL PRODUCTS

This application is A 371 of PCT/US94/14638 filled Dec. 20, 1994.

This invention relates to a new method for preparing solid pharmaceutical compositions for oral administration of low-dose medications whose active ingredients have steroidal or steroid-like structures.

BACKGROUND OF THE INVENTION

The pharmaceutical art recognizes that, when highly active medicaments are prepared in pharmaceutical form for administration to subjects in need of therapy, the even distribution of active ingredient throughout the carrier is important for insuring a proper dosage and no toxic effects due to hot spots of drug. The problem is especially applicable to low dose steroidal compounds; for example, estrogens, progestins, digitalis, spironolactone. These are known to migrate through the carrier upon drying.

The prior art of low dose pharmaceutical formulation is illustrated in the literature for estrogen (e.g., estradiol). Much of the prior art comprises broad disclosures of standard preparative methods; for example, Pasquale, U.S. Pat. No. 4,544,554, etc., or Lerner, U.S. Pat. No. 3,568,828, with no mention of the problem of non-uniform distribution. The latter reference describes the preparation of low dose drugs using conventional wet granulating methods with organic solvents such as chloroform.

DeHaan (Akzo), European Patent Application No. 92103963.2, discusses the problem of uneven distribution of low dose medicaments in solid pharmaceutical dose units. This, as stated above, may be due in part to migration of the medicament. DeHaan further states that liquid granulation methods for preparing solid dosage units of low dose medicaments are also not acceptable because of the cost and environmental handicaps of the organic solvents which are unacceptable for this use.

DeHaan suggests an alternative method of manufacture which uses the compression of a dry solid mix containing an excipient having a prescribed binding-demixing ratio of the medicament to excipient.

There remains a need in the art for other methods of preparing solid dosage forms, mainly tablets of low-dosage medicaments, which can be adapted by manufacturing pharmaceutical companies to available equipment.

SUMMARY OF THE INVENTION

This invention relates to a method for preparing solid pharmaceutical dosage units containing low dose active ingredients using a wet granulation technique which employs aqueous solvents and applicable surfactants.

DETAILED DESCRIPTION OF THE INVENTION

This method utilizes an aqueous medium which contains the active ingredient or ingredients, a quantity of one or more surfactants sufficient to dissolve or suspend said active ingredients uniformly throughout the medium and other manufacturing additives as known to the art. The latter include granulating-binding agents such as gelatin; natural gums, such as acacia, tragacanth; starches, sodium alginate, sugars, polyvinylpyrrolidone; cellulose derivatives such as hydroxypropylmethylcellulose, polyvinyloxoazolidones; pharmaceutical fillers such as lactose, microcrystalline cellulose, dicalcium phosphate, tricalcium phosphate, calcium sulfate, dextrose, mannitol, sucrose; tabletting lubricants if needed such as calcium and magnesium stearate, stearic acid, talc, sterotex (alkaline stearate).

The components are granulated, the resulting granules are dried, sieved and compressed into tablets or filled into capsules. Other oral product forms may be similarly prepared by art methods such as chewable tablets, lozenges, troches, sustained or delayed release products or suspensions.

The active ingredients comprise any medicament which has a low effective dose such as those below 10 mg per dosage unit. Most useful are those medicaments having a steroidal nucleus, the cyclopentanoperhydrophenanthrene ring system, in their chemical structures such as the estrogens or progestins.

Examples of the former are ethinylestradiol, estrone, mestranol, 17-alpha-ethinyl estradiol-3-methylether esterified estrogens, and, especially estradiol, methyl testosterone. The dosage amounts and indications of these and other active ingredients are those described in the literature such as the Physician's Desk Reference.

The progestins are 3-ketodesogestrel, desogestrel, levodesogestrel, norgestrel, gestodene, mestranol, norethindrone, norethindrone acetate.

Other medications known to the art which are used in low doses are spironolactone, digoxin, glipizide, estazolam, clorazepate dipotassium, albuterol sulfate, clonidine HCL, alprazolam.

The term "aqueous medium" for the second ingredient of this invention is used within the custom of the pharmaceutical art. Primarily, it connotes a water medium, with added water-miscible solvents such as isopropanol or ethanol when needed, to support the active ingredient or pharmaceutical aids.

The third ingredient of the critical step of this invention is a surfactant acceptable in pharmaceutical manufacturing practice and selected from the three categories of surfactants: cationic, anionic and non-ionic compounds. Exemplary of useful surfactants are sodium lauryl sulfate, sorbitan monolaurate, sorbitan monostearate, polysorbate 80, polysorbate 60, poloxamer 407, poloxamer 188 (polyoxethylene, polyoxypropylene block polymers), polyoxyl 20 cetostearyl ether, dioctyl sodium sulfosuccinate, dioctyl calcium sulfosuccinate, nonoxynol, benzalkonium chloride, sorbitan monooleate.

The quantity of surfactant in the granulating mixture is enough to be non-toxic and to support the steroidal active ingredient in solution or suspension. Usually, this means very small, almost catalytic, quantities, such as less than 0.01% by weight. Applicant has devised a simple test procedure for determining the applicability of a selected surfactant for this process. Details are presented below.

Other pharmaceutically acceptable additives are used in the first step granulation but are not considered critical to this invention. These include binding-granulating agents such as polyacrylamides, polyvinyloxoazolidones, sucrose, and sodium carboxymethylcellulose; fillers such as lactose, talc, cellulosics, dibasic calcium phosphate, starches; disintegrants if a tablet or capsule is formed, such as croscarmellose sodium, starch, sodium carboxymethyl starch, veegum, ion exchange resins (amberlite), sodium bicarbonate; or lubricants for tablet compression such as polyethylene glycol 4000 and 5000, hydrogenated vegetable oils, light mineral oil.

The practice of this invention depends on the novelty and practical benefits of using a low dose medicament, a pharmaceutically acceptable quantity of surfactant and an aqueous medium. The preferred ingredients are estradiol, sodium lauryl sulfate and water from a povidone solution. The final product form is a tablet containing 2.00 mg of medicament per tablet. The therapeutic utility is demonstrated by oral administration of such a dosage unit from 1–5 times daily to a subject in need of treatment, for example for menopausal abnormalities.

In practice, the estradiol is suspended in a 1% povidone solution containing a trace (0.005%) of surfactant. The aqueous suspension is blended with fillers and granulated in a granulating vessel. The granulation is dried, screened and blended with fillers, disintegrants and lubricants. The granulation is then compressed into tablets.

Alternatively, the dried granules may be filled into a capsule. Where extended or delayed release of the low dose medicament is desired the granules or capsule may be coated as known to the art.

The following examples are designed to teach the operation of this invention.

Example 1
ESTRADIOL 2 mg TABLETS
Formula

| Materials | Percent | Mg/Tablets |
| --- | --- | --- |
| Microcrystalline Cellulose (Avicel PH102), NF | 20.00 | 32.80 |
| Lactose 316 (Fast Flo), NF | 51.94 | 85.18 |
| Dibasic Calcium Phosphate (Cal-Star), USP | 23.70 | 38.87 |
| Colloidal Silicone Dioxide (Cab-o-sil), NF | 1.00 | 1.64 |
| Croscarmellose Sodium (Ac-Di-Sol), NF | 1.00 | 1.64 |
| Magnesium Stearate | 1.00 | 1.64 |
| Povidone K92-32, NF | 0.14 | 0.23 |
| Sodium Lauryl Sulfate, NF | 0.0003 (Trace) | Trace |
| Estradiol, USP | 1.22 | 2.00 |

Procedure
1. Suspend the estradiol in a 1% povidone solution in which 0.005% sodium lauryl sulfate has been dispersed.
2. Blend the Cal-Star and lactose until homogeneous.
3. Granulate the blend from Step 2 with the suspension of estradiol in povidone solution from Step 1.
4. Dry the above granulation.
5. Screen and blend the dried granulation from Step 4 with the other ingredients.
6. Compress the blend from Step 5 into 164 mg tablets. Each tablet containing 2 mg of estradiol.

EXAMPLE 2

Protocol for Screening Surfactant for Low Dose Drug Suspensions

I. Prepare a 1% povidone stock solution in water.
II. Prepare reference solution of 1% povidone—0.005% sodium lauryl sulfate (SLS).
  A. Prepare a 14.3% w/w solution with the SLS solution and estradiol.
  B. Prepare a 14.3% w/w solution with the SLS solution and spironolactone.
  C. Compare the estradiol solution and the spironolactone solution. If they have the same appearance, spironolactone can be used as the model drug and estradiol can be used for a check.

III. Use the stock povidone solution to prepare solutions with the other surfactants to be investigated, such as, but not limited to, dioctyl sodium sulfosuccinate, dioctyl calcium sulfosuccinate, nonoxynol, benzalkonium chloride, sorbitan monooleate.
  A. Prepare 1% povidone—1% surfactant solutions.
    1. Prepare 14.3% w/w solution with the surfactant and the steroidally derived drug.
    2. Compare to reference solution.
    3. If the surfactant/steroidal solution conforms to the reference solution:
      a. Dilute surfactant solution with 1% povidone solution in 0.5% increments.
      b. Determine the lowest concentration of surfactant that a flocculated suspension can be formed.

What is claimed is:

1. A process for making pharmaceutical dosage units containing a therapeutic quantity of one or more low dosage medicinal agents comprising the steps of;
(a) preparing an aqueous medium comprising one or more pharmaceutically acceptable surfactants, wherein the quantity of said surfactant or surfactants is sufficient to support said medical agent in solution; and
(b) granulating said one or more low dosage medicinal agents in said aqueous medium to form a granulation.

2. The process of claim 1 wherein one or more low dosage medicinal agent has a steroidal structure.

3. The process of claim 2 wherein said medicinal agent is an estrogen and, optionally, a progestin.

4. The process of claim 3 wherein said estrogen is estradiol or esterified estrogens.

5. The process of any one of claims 1, 2, 3, and 4 wherein the aqueous medium is water and said surfactant is sodium lauryl sulfate.

6. The process of claim 5 wherein the product form made by said process is a tablet.

7. A pharmaceutical composition made by the process as claimed in any one of claims 1, 2, 3, 4, 18, 21, 22, 25, or 26.

8. A pharmaceutical composition as claimed in claim 7 wherein the aqueous medium is water and the surfactant is sodium lauryl sulfate.

9. A pharmaceutical composition comprising a therapeutic quantity of one or more low dosage medicinal agent and one or more pharmaceutically acceptable surfactant in an aqueous medium and, optionally, one or more manufacturing additives and binding-granulating agents.

10. The composition of claim 9 wherein said one or more low dosage medicinal agent has a steroidal structure.

11. The composition of claim 10 wherein said medicinal agent is an estrogen and, optionally, a progestin.

12. The composition of claim 11 wherein said estrogen is estradiol or esterified estrogens.

13. The composition of any one of claims 9 to 12 wherein the aqueous medium is water, water from a povidone solution, or water and a water-miscible solvent.

14. The composition of claim 13 wherein said composition is in the form of a tablet, lozenge, troche, or capsule.

15. The composition of claim 14 wherein said composition is in the form of a tablet.

16. The composition of claim 13 wherein said surfactant is sodium lauryl sulfate.

17. The composition of claim 15 wherein said surfactant is sodium lauryl sulfate.

18. A method for evenly distributing the active ingredient of a low dosage medicinal agent in a pharmaceutically acceptable carrier comprising:
(a) preparing an aqueous medium comprising one or more pharmaceutically acceptable surfactants, wherein the quantity of said surfactant or surfactants is sufficient to support said medicinal agent in solution; and (b) granulating said active ingredient in said aqueous medium to form a granulation.

19. A method of claim 18 wherein said medicinal agent is an estrogen and, optionally, a progestin.

20. A method of claim 19 wherein said medicinal agent is estradiol.

21. The process of claim 1, wherein said quantity of said one or more pharmaceutically acceptable surfactants is less than 0.01% by weight of said granulation.

22. The process of claim 21, wherein the quantity of said one or more pharmaceutically acceptable surfactant is not more than 0.005% by weight of said granulation.

23. The composition of claim 9 wherein said quantity of said one or more pharmaceutically acceptable surfactants is less than 0.01% by weight of the composition.

24. The composition of claim 23 wherein the quantity of said one or more pharmaceutically acceptable surfactant is not more than 0.005% by weight of the composition.

25. The process of claim 1, further comprising the step of processing said granulation into a tablet or capsule dosage unit.

26. The process of claim 18, further comprising the step of processing said granulation into a tablet or capsule dosage unit.

* * * * *

UNITED STATES PATENT AND TRADEMARK OFFICE
CERTIFICATE OF CORRECTION

PATENT NO. : 5,976,570
DATED      : November 2, 1999
INVENTOR(S) : Greaves, et. al.

It is certified that error appears in the above-identified patent and that said Letters Patent is hereby corrected as shown below:

Claim 1, col. 4, line 18, change ";" to -- : --.

Claim 1, col. 4, line 22, change "medical" to -- medicinal --.

Claim 5, col. 4, line 31, change "said" to -- the --.

Signed and Sealed this

Twenty-fifth Day of July, 2000

Attest:

Q. TODD DICKINSON

*Attesting Officer*        *Director of Patents and Trademarks*